(12) United States Patent
Lorenzo et al.

(10) Patent No.: US 7,812,125 B2
(45) Date of Patent: Oct. 12, 2010

(54) CARTILAGE INTERMEDIATE LAYER PROTEIN 2 C1 AND ITS USE TO DIFFERENTIATE OSTEOARTHRITIS FROM RHEUMATOID ARTHRITIS AND NON-DISEASE CONDITIONS

(75) Inventors: Pilar Lorenzo, Lund (SE); Tore Saxne, Lund (SE); Dick Heinegard, Lund (SE)

(73) Assignee: Anamar Medical AB, Gothenburg (SE)

( * ) Notice: Subject to any disclaimer, the term of this patent is extended or adjusted under 35 U.S.C. 154(b) by 212 days.

(21) Appl. No.: 11/728,857

(22) Filed: Mar. 27, 2007

(65) Prior Publication Data

US 2008/0241851 A1 Oct. 2, 2008

(51) Int. Cl.
C07K 14/00 (2006.01)
C07K 16/00 (2006.01)
A61K 35/12 (2006.01)
A61K 35/32 (2006.01)
A61K 38/00 (2006.01)

(52) U.S. Cl. ............... 530/350; 424/520; 424/549; 530/324; 530/388.15

(58) Field of Classification Search ............... None
See application file for complete search history.

(56) References Cited

U.S. PATENT DOCUMENTS

| 5,876,963 | A | 3/1999 | Mitchell et al. |
| 6,124,095 | A | 9/2000 | Magna et al. |
| 6,251,389 | B1 * | 6/2001 | Magna et al. ............ 424/94.6 |

OTHER PUBLICATIONS

Bowie et al (Science, 1990, 257:1306-1310).*
Greenspan et al. (Nature Biotechnology 17: 936-937, 1999).*

* cited by examiner

Primary Examiner—Vanessa L. Ford
(74) Attorney, Agent, or Firm—Lynn E. Barber (57) ABSTRACT

A method for differentiation of osteoarthritis from rheumatoid arthritis and non-disease conditions in a sample, comprising measuring in the sample the concentration of human cartilage intermediate layer protein 2(CILP-2) in body fluids and more specifically, measuring in the sample the concentration of the N-terminal part of CILP-2 (2C1) or fragments thereof.

1 Claim, 2 Drawing Sheets

CARTILAGE INTERMEDIATE LAYER PROTEIN 2 C1 AND ITS USE TO DIFFERENTIATE OSTEOARTHRITIS FROM RHEUMATOID ARTHRITIS AND NON-DISEASE CONDITIONS

FIELD OF INVENTION

The present invention relates to a method aiding in the assessment of osteoarthritis (OA). The method especially is used in assessing the absence or presence of osteoarthritis. The method is for example practiced by analyzing biochemical markers, comprising measuring in a sample the concentration of human cartilage intermediate layer protein 2 (CILP-2) in body fluids and correlating the concentrations determined to the absence or presence of osteoarthritis. More specifically, the present invention is related to the N-terminal part or cartilage intermediate layer protein 2 C1 or fragments thereof. This invention also describes development of diagnostic and prognostic assays for differentiation of osteoarthritis from rheumatoid arthritis (RA) and non-disease conditions.

BACKGROUND

Arthritis is a group of conditions that affect the health of the joints in the body, including rheumatoid arthritis and psoriatic arthritis, which are autoimmune diseases; septic arthritis, caused by joint infection; and the more common osteoarthritis. Unlike the autoimmune diseases, osteoarthritis largely affects older people and results from the degeneration of joint cartilage.

Osteoarthritis is the most common form of arthritis affecting a large part of the population. Although osteoarthritis can affect almost any joint, it most often affects the hands, knees, hips, and spine. Common symptoms include pain, stiffness, loss of joint motion, and changes in the shape of affected joints. It is frequently called degenerative joint disease or "wear and tear" arthritis. Although it can be brought on suddenly by an injury, its onset is generally gradual; aging brings on a breakdown in cartilage, and pain gets progressively more severe, although in early stages it can be relieved with rest. Dull, throbbing nighttime pain is characteristic, and it may be accompanied by muscle weakness or deterioration. Symptoms usually appear after the age of 50 and progress slowly. Starting with joint pain, the condition progresses and eventually the joint becomes deformed, limiting movement. As the cartilage breaks down it leaves the bone exposed altering gait. Later stages of the disease have been shown to have a component of inflammation, where the process in the cartilage may have a role in stimulating this inflammation. The condition is believed to be initiated by excessive or unusual load on the joint, where overweight, poor posture, repetitive strain from work, injury, sports injury or a combination of these factors are known to increase the risk.

Osteoarthritis also includes new production of tissue structures, particularly evident in the form of the so-called osteophytes that are new structures formed by endochondral bone formation. Although mechanical factors appear to have a role in both disease initiation and progression, little is known about specific events, partly due to the lack of diagnostic procedures that can identify those early stages of the disease. Patients usually seek care due to pain and the joint malfunction late in disease development, when cartilage destruction has already advanced significantly.

Today there is no single sign, symptom, or test result that allows a definitive diagnosis of osteoarthritis. Instead, the diagnosis is based on consideration of several factors, including presence of the characteristic signs and symptoms of osteoarthritis and the results of laboratory tests and x-rays, criteria set by The American College of Rheumatology (ACR).

Radiographs can usually confirm the diagnosis of osteoarthritis, although the findings are nonspecific. The cardinal radiographic features of the disease are loss of joint space and presence of new bone formation or osteophytes. The association between joint pain and radiographic features of osteoarthritis is not very close, such that even joints with pathologic or radiographic evidence of this disease may remain asymptomatic. Another shortcoming of using radiography for depicting the level of cartilage destruction in OA, particularly for the knee, is the necessity to have the exact angle of the X-rays for a correct measure of the joint space. Diagnosis using X-rays is used several years after the onset of the injury, whereas bio-markers, such as cartilage intermediate layer protein 2 C1 and fragments thereof can be used much earlier for proper diagnosis.

It is not clear what the underlying process in the progressive tissue destruction of osteoarthritis is, but there are clear events of breakdown of the major tissue macromolecules caused by increased proteolytic activity. It has been shown that the early event in this progressive tissue destruction is degradation of aggrecan (a proteoglycan that is a major structural component of cartilage), where five specific sites along the molecule can be cleaved by the so-called aggrecanases (ADAMTS-4 and 5). However, the normal levels of aggrecan are adapted to e.g. altered mechanical load on the cartilage in a process that involves cleavage of the molecule at the typical sites and by the same ADAMTS-enzymes. There is fragmentation of collagen accomplished by specific collagenases and other enzymes that will degrade major molecules like cartilage oligomeric matrix protein (COMP).

In the process of osteoarthritis some of the fragments that are produced are no longer retained in the tissue and are released into the surrounding body fluids and may eventually reach the circulation. New technology is based on measuring such fragments in body fluids as an indicator of the active process leading to tissue destruction. This molecular marker technology offers possibilities for new diagnostic procedures. These have the potential to detect much earlier events in the tissue destruction than is possible with the currently used approaches. It has been observed that when increased levels of circulating COMP fragments that have been released into synovial fluid eventually reach the blood, they can be used as a prognostic indicator of the process that will lead to destruction of the articular cartilage as observed by x-ray imaging. Although the processes in the diseases of osteoarthritis and rheumatoid arthritis are different, it appears that the serum COMP levels have a prognostic value in both cases.

One limitation in evaluating the significance of altered COMP-levels in body fluids is the difficulty in distinguishing whether the majority of the COMP detected originates from normal turnover or disease progression. Other indicators that have been utilized include the C-terminal telo-peptide released upon cleavage of collagen type II, (referred to as CTX-II). Other assays directly measure new ends within the original polypeptide chain that are formed when collagen type II is cleaved by collagenases. An assay directed at the repair phase makes use of release of the C-terminal propeptide of collagen type II (CP-II) when procollagen is processed for collagen fibrillogenesis. This propeptide is apparently not retained in the cartilage. The inventors have found that procedures to measure release of aggrecan fragments have limited use, since the major fragments containing the negatively charged chondroitin sulfate chains appear to be largely eliminated in the lymph nodes without reaching the circulation. However, measurements of aggrecan fragments in synovial fluid from patients with early rheumatoid arthritis have proven to identify those patients that develop more extensive cartilage destruction over a 10 year period (1).

One obvious shortcoming of all these markers is the lack of specificity for a given joint disease and overlap of measured levels between samples from normal individuals and those with joint disease. Furthermore there is no or little distinction observed between cases with rheumatoid arthritis and osteoarthritis with any of these indicators. Only a portion of patients show values sufficiently elevated to clearly distinguish them from normal individuals (2).

One issue is that there is a continuous turnover of tissue structural molecules in response to regular and frequent load. This serves to adapt tissue function to new requirements, including removing fatigued tissue elements. One consequence of this turnover is that there is a continuous release of fragments generated by these normal cleavages. In assays used today of fragments as molecular indicators there is little distinction between those generated by normal turnover and those generated by a pathological process. Thus there is a high background, which hampers the ability to detect an increased pathological molecular process. It is however possible that some of the collagen type II (collagen, abundant in articular cartilage) breakdown products may distinguish more clearly between normal and pathological events, even if the process may be induced by the same enzyme. This is possible since normal collagen turnover as shown for articular cartilage is orders of magnitude slower than for other matrix constituents.

As used herein, the proteins where cartilage Intermediate Layer Protein precursor is referred to as CILP-1 and CILP-2 respectively. The N-terminal part that we study is referred to as cartilage intermediate layer protein 2 C1, which is distinct from cartilage intermediate layer protein 2 C2.

Cartilage intermediate layer protein (CILP), a large secreted glycoprotein (3-6) is thought to play a role in cartilage scaffolding (7) has also been claimed to have nucleoside triphosphate pyrophosphohydrolase [NTPPPH] activity (8-11). The expression of CILP appears to be largely restricted to cartilage (3, 4, 9, 11, 12). The amount of CILP protein increases in aging human articular cartilage, and CILP is one of only a few cartilage matrix proteins whose expression becomes markedly up-regulated in early osteoarthritis (4). In normal cultured porcine chondrocytes, transforming growth factor β1 (TGFβ1) induces CILP expression, whereas insulin-like growth factor 1 (IGF-1) suppresses CILP expression (10). The originally detected CILP, is now referred to as cartilage intermediate layer protein 1 C1 (UniProtKB/Swiss-Prot entry O75339).

In the nucleotide sequence of a protein cartilage intermediate layer protein 2 (CILP-2 was deposited in the Genbank sequence databank (Accession AF542080, year 2002). The first study of the protein CILP-2 appeared in 2003 (13), when it was found that it did not show nucleotide pyrophosphatase phosphodiesterase(NPP) activity (13).

CILP-2 has a 50% homology to CILP-1 and their data indicate that it is similarly cleaved into corresponding cartilage intermediate layer protein 2 C1 and cartilage intermediate layer protein 2 C2. (UniProtKB/Swiss-Prot entry Q8IUL8). From proteomics approaches both proteins are found in cartilage extracts.

In recent work we have shown upregulation in both early and late stages of osteoarthritis of production of COMP, fibronectin and at the same time new protein that we characterized and named CILP, now cartilage intermediate layer protein 1 C1 (3, 4, 16).

The peptide covering the amino acids 21-709 (SEQ ID NO: 1), of the human CILP-2 has now by the inventors of this patent application surprisingly been shown to be a marker which can be used to for differentiation of osteoarthritis from rheumatoid arthritis and non-disease conditions.

Studies implicate CILP (cartilage intermediate layer protein 1 C1) as an autoantigen in patients with osteoarthritis (14, 15). There are no studies known to indicate that cartilage intermediate layer protein 2 C1 may be altered in osteoarthritis. No article or patent could be found to show or suggest that cartilage intermediate layer protein 2 C1 or fragments thereof, may be used in the diagnosis of osteoarthritis.

Work by Du et al 2005 (14) implicated that a small proportion of patients with knee osteoarthritis had auto antibodies to CILP (cartilage intermediate layer protein 1 C1). Antibodies were only detected in 25/136 of the osteoarthritis patients. Similarly Tsuruha et al. 2001 (7) detected only 8-10, 5% antibodies to different regions of CILP (cartilage intermediate layer protein 1 C1). No studies have been reported to indicate antibodies to cartilage intermediate layer protein 2 C1 or fragments thereof, the protein that is the topic of this invention.

In U.S. Pat. No. 6,124,095 and U.S. Pat. No. 6,251,389 assigned to Incyte, CILP-2 and polynucleotide encoding CILP-2 are disclosed. In these patents, the protein is denominated human nucleotide pyrophosphohydrolase-2 (NTPPH-2), but the NTPPH-2 sequence is identical to CILP-2. They noted the expression of NTPPH-2 in rheumatoid and osteoarthritic synovial capsule. This patent does not describe the possibility of using NTPPH-2 for selective identification of osteoarthritis patients. The same applicant has a granted patent (U.S. Pat. No. 5,876,963) on CILP-1 (NTPPH-1) and polynucleotide encoding NTPPH-1.

DE 10328033 (S. Blaess) describes chip carrying DNA sequences associated with osteoarthritis and rheumatoid arthritis e.g. for diagnosis, monitoring and drug development. They do not mention cartilage intermediate layer protein 2 C1.

WO03/054166 (Incyte) describes methods for determining susceptibility of an individual, preferably an osteoarthritis patient, to joint space narrowing and/or osteophyte development and/or joint pain comprising identifying whether the individual has at least one polymorphism in a polynucleotide encoding a protein, one of many proteins mentioned is CILP. However they do not mention cartilage intermediate layer protein 2 C1.

WO02/095415 and WO01/38872 (Osteometer Biotech) both describe an assay for the diagnosis of the severity of osteoarthritis or rheumatoid arthritis comprising detecting an isomerized or optically inverted protein or fragment of a protein in a sample. Neither the fragment described in WO02/095415 or protein WO01/38872 is from cartilage intermediate layer protein 2 C1.

WO01/20018 (Univ. of California) describes a method for identifying a risk for an arthritic disorder, e.g. osteoarthritis, comprising comparing the level of at least one indicator, e.g. NTPPH, of altered mitochondrial function in a biological sample with a control sample.

Proper diagnosis of osteoarthritis is currently possible only at advanced disease and depends on X-ray and clinical investigations. In the case of rheumatoid arthritis destruction of the joint cartilage can only be determined at advanced stages by X-ray.

RA can worsen very quickly in its early stages and serious damage to the joints may occur in as short a time span as 24 months. When modern, effective treatments for RA, such as blocking TNF-α activity are initiated early, symptoms can be relieved and the worsening of joint destruction slowed, and early disability can be avoided.

There is no documented disease modifying treatment of osteoarthritis. At present, no cure is available and treatment focuses on relieving pain. Common treatments include the use of non-steroidal anti-inflammatory drugs (NSAID's), which are often used to relieve pain Compounds such as chondroitin and glucosamine are thought to improve the cartilage itself, but well controlled studies remain an important focus.

In severe cases, joint replacement often becomes necessary. In a few cases joints may be fused. This procedure stops the pain, but results in permanent loss of joint function. Another treatment, not yet used for fully developed osteoarthritis, includes the transplantation of cultured autologous chondrocytes. If the condition persists without correction and/or therapy, the joint is destroyed, leading to major replacement surgery with total prosthesis, or to disability.

Thus, to introduce new therapeutic regimens that may stop the early stages of disease development, new, early and correct diagnosis is of essence and would provide a breakthrough. For this reason the inventors of this application attempted to develop an assay that can be used as an indicator for developing osteoarthritis, as well as for differentiation of osteoarthritis from rheumatoid arthritis as well as a normal joint.

In early experiments the inventors could show that cartilage intermediate layer protein 1 C1, although upregulated in osteoarthritis, including both the early and late stages, did not show a marked increase in synovial fluid from patients with osteoarthritis and was not significantly different in fluid from patients with rheumatoid arthritis. Upon proceeding to develop an assay for cartilage intermediate layer protein 2 C1, we surprisingly showed that this protein acted as an indicator that showed unexpected and uniquely elevated levels in osteoarthritis. Levels in serum and synovial fluid are highly elevated and show no overlap with samples from rheumatoid arthritis and normal individuals. This is the first time that an assay for any protein released from a tissue have shown such a difference between samples representing different joint disease categories. The invention herein provides a novel diagnostic and prognostic assay for the detection of the osteoarthritic process prior to as well as at the time when diagnosis can be established. Other objects and advantages will be more fully apparent from the following disclosure and appended claims.

SUMMARY OF THE INVENTION

The invention provides a method for differentiation of osteoarthritis from rheumatoid arthritis and non-disease conditions in a sample, comprising measuring in the sample the concentration of the cartilage intermediate layer protein 2 C1 protein or fragments thereof.

DETAILED DESCRIPTION OF THE INVENTION AND PREFERRED EMBODIMENTS THEREOF

The work with respect to the invention herein is based on early data on cartilage intermediate layer protein 1 C1, which we identified as one of a few proteins showing a major increase in osteoarthritis. Our first attempt with our antibody raised against the protein purified from the tissue was promising indicating that the protein was released into the synovial fluid from osteoarthritis patients and that the highest level was found in a sample from an osteoarthritis patient.

Work with the recombinant cartilage intermediate layer protein 1 C1 produced in EBNA 293 fibroblasts confusingly showed that this pure protein as the coating antigen in ELISA did not result in good inhibition levels with synovial fluid samples. At this time cartilage intermediate layer protein 2 appeared in the databases and we suspected that there was a contamination of antibodies to this protein in our preparation. We therefore developed a specific antibody to cartilage intermediate layer protein 2 C1, and have now used this to develop an assay for fragments of this protein in synovial fluid and serum. This assay turned out to be very promising and analyses of serum samples from normal individuals as well as patients with rheumatoid arthritis and osteoarthritis gave the results depicted in FIG. 1.

Figure 1:
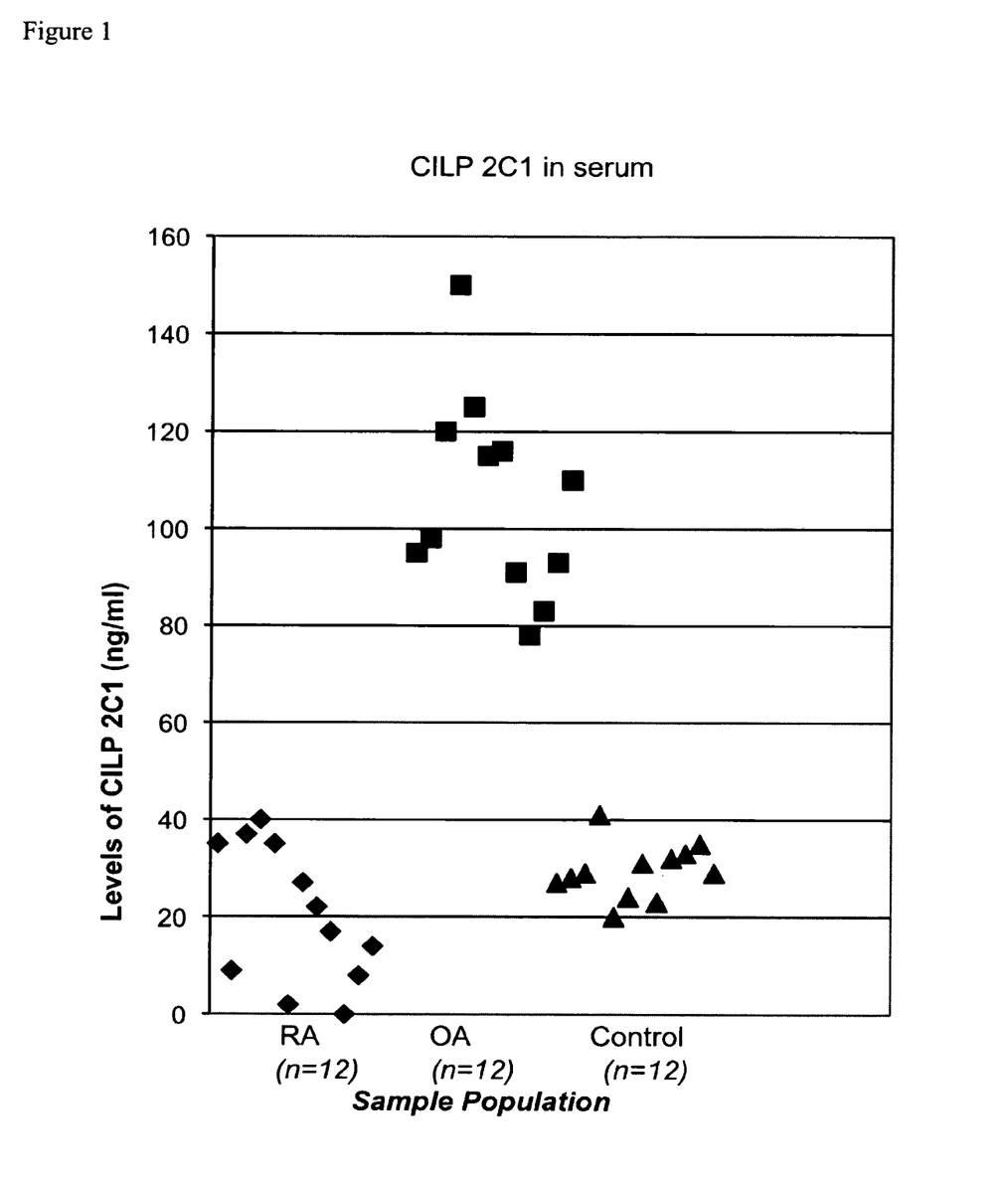
FIG. 1 is a graph depicting the levels of CILP 2C 1 protein in ng/ml in samples obtained from normal control serum from blood donors (black triangles), serum from patients with osteoarthritis (black squares) and serum samples from patients with knee joint rheumatoid arthritis (black diamonds). Competitive ELISA, using a specific antibody to CILP 2C1, was used to analyze the serum samples. The Microwin 200 software program was used to evaluate the absorbance values obtained at 450 nm and to calculate the content of CILP 2C1 in the samples. Each point represents the mean of duplicate measurements corresponding to each patient.
Figure 2:
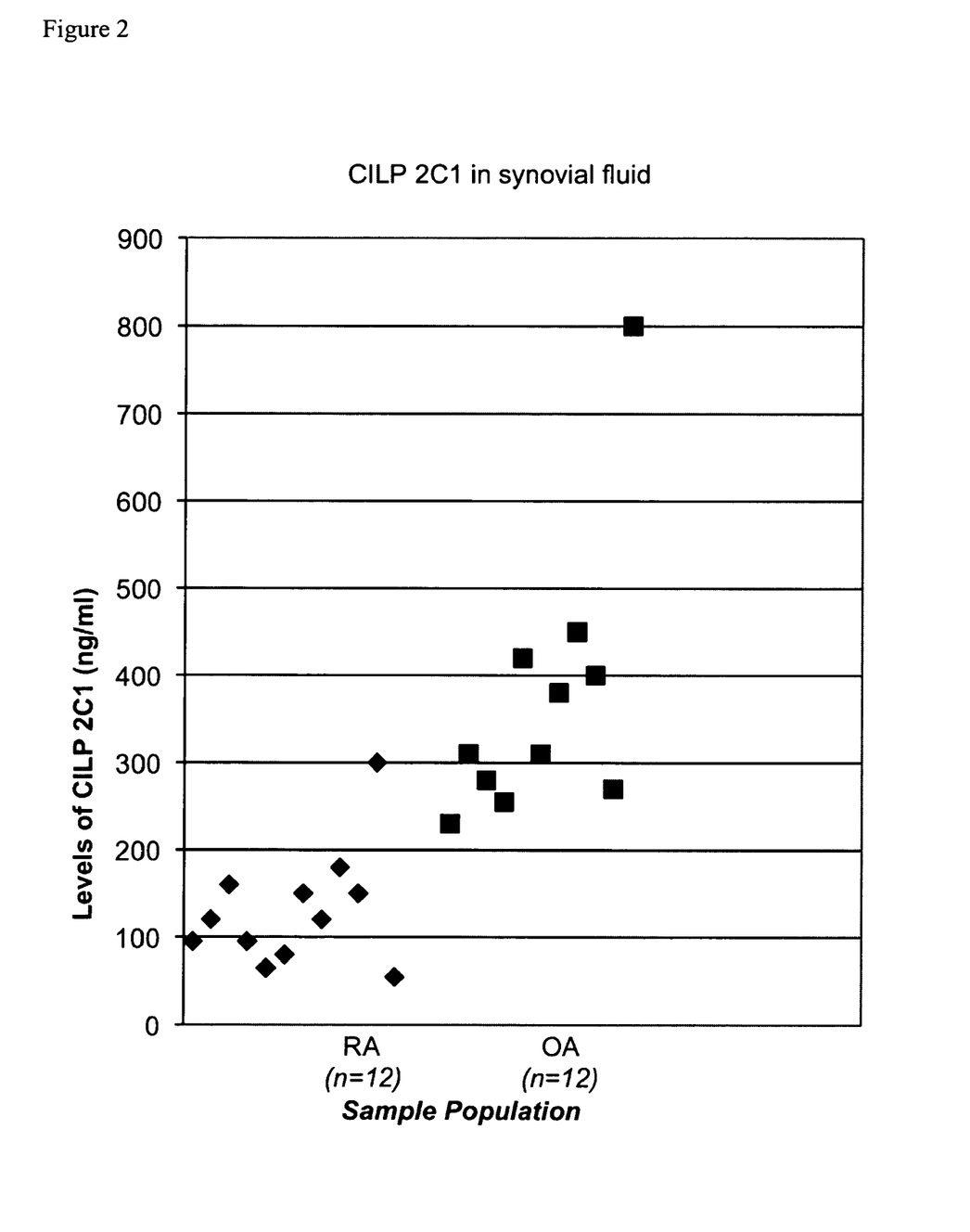
FIG. 2 is a graph depicting the levels of CILP 2C1 protein in ng/ml in knee joint synovial fluid samples obtained from patients with osteoarthritis (black squares) and synovial fluid from patients with knee joint rheumatoid arthritis (black diamonds). Competitive ELISA, using a specific antibody to CILP 2C1, was used to analyze the samples. The Microwin 200 software program was used to evaluate the absorbance values obtained at 450 nm and to calculate the content of CILP 2C1 in the samples. Each point represents the mean of two determinations corresponding to each patient.

The results showed that the levels cartilage intermediate layer protein 2 C1 were much higher in osteoarthritis compared to both rheumatoid arthritis and normal individuals, with no overlap. This is the first time that an assay has shown such a difference between samples representing different joint disease categories for any protein released from a tissue.

Serum and synovial fluid samples from twelve patients with clinically established rheumatoid arthritis according to the ACR-criteria (all with knee joint arthritis), twelve patients with clinically established knee joint osteoarthritis according to the clinical and radiographic ACR-criteria and twelve normal control serum samples from blood donors were analyzed with the established ELISA procedure. A central observation was that the levels of cartilage intermediate layer protein 2 C1 or fragments thereof were distinctly higher in the samples from patients with osteoarthritis, with no significant overlap to levels in the normal individuals, which in turn showed levels very similar to those in samples from patients with rheumatoid arthritis. The patients with osteoarthritis showed a wider range of considerably higher levels demonstrating that the release of increased levels of cartilage intermediate layer protein 2 C1 was a common denominator for this group.

The results show a unique difference in molecular marker levels between different conditions affecting the joint. Interestingly abundant data show that COMP levels in serum show elevated levels both in rheumatoid arthritis and osteoarthritis. Therefore ratios between COMP and cartilage intermediate layer protein 2 C1 distinguish individuals with rheumatoid arthritis from those normal, particularly in the subgroup of patients that appeared to show subnormal levels of cartilage intermediate layer protein 2 C1 or its fragments.

The results show a novel molecular marker that has the potential to serve in the diagnosis of conditions with osteoarthritis. Levels of cartilage intermediate layer protein 2 C1 are distinctly higher than in normal individuals and in patients with rheumatoid arthritis. The difference between levels in normal individuals and those with osteoarthritis indicate that the assay of cartilage intermediate layer protein 2 C1 also serves as an indicator of existing disease activity. The wide range of values in patient samples indicates that the level correlates to the intensity of the process. Samples that may be analyzed by the method of the invention include synovial fluid, blood, plasma, serum and urine.

Example 1

Preparation of the Antigen and Antiserum

A synthetic peptide within the amino acids 21-709 (SEQ ID NO: 1), of the human CILP-2 (GeneBank accession nr. Q8IUL8) was used as immunogen. An additional cysteine residue was added at the amino termini to allow selective coupling to different substrates. The peptide sequence (SEQ ID NO: 1) was used as immunogen after conjugation in its N-terminal via an added cysteine to keyhole limpet hemocyanin (KLH) for the production of polyclonal antibodies according to standard protocols. Any fragment in the range of amino acids 21-709, of the human cartilage intermediate layer protein 2 C1 could be used as an immunogen.

A commercial source (Innovagen AB, Lund, Sweden) was used for the synthesis of the peptide, the conjugation to a carrier, the preparation of the antigen for immunization, including the injection to the rabbit and the production of the antiserum.

Example 2

Purification of the Anti Peptide Antibody from the Crude Antiserum

The generated antiserum was affinity purified on a column with the immobilized cartilage intermediate layer protein 2 C1 peptide, (Innovagen AB, Lund, Sweden). The column (1.5 ml gel) was equilibrated with phosphate buffered saline (PBS, 0.1 M phosphate buffer, 150 mM NaCl, pH 7.5) and 5 ml of serum were applied and incubated end over end for 1 hour at room temperature then further incubated for 1 hour without mixing. The column was washed with 15 and then with 10 ml PBS containing 1 M NaCl. The column was eluted step wise with 1.5 ml of 100 mM Glycine pH 2.7. Ten fractions were collected and neutralized immediately with 50 µl of 1M Tris pH 9.5. Fractions with the highest absorbance were pooled and dialyzed against PBS containing 0.05% sodium azide. After dialysis the volume was measured and the concentration of the IgG was determined by it OD at 280 nm. The affinity purified antibody, stored frozen at −20° C. in 200 µl aliquots, was used in all the assays.

Example 3

Competitive Enzyme Linked Immunosorbent Assay (ELISA) for Cartilage Intermediate Layer Protein 2 C1

A specific competitive ELISA was developed to measure human cartilage intermediate layer 2 C1 in body fluids.

1. Biotinylation of the peptides: Peptides were biotinylated via their terminal cysteine with EZ-Link®Maleimide PEO$_2$-Biotin as described by the manufacturer (PIERCE).

2. Pre-treatment of the antibody: The affinity purified peptide antibody was diluted 1:50 in phosphate buffered saline (PBS), pH 7.4 containing 5% n,n-dimethylformamide (Sigma-Aldrich). After incubation for 1 hour at room temperature the antibody was diluted to 1:2000 with 4% Triton in 10 mM phosphate (NaH$_2$PO$_4$) pH 7.5.

3. Pre-treatment of the standard and samples: Standard (from 1 to 125 ng/ml) in 1% (w/v) sodium dodecyl benzene sulfonate (SDBS, Sigma-Aldrich) in 0.1 M sodium chloride, 0.05 M sodium phosphate pH 7.5 containing 0.5% bovine serum albumin (BSA, Sigma-Aldrich) and an appropriate dilution of synovial fluids or sera in 1% (w/v) SDBS solution without BSA were incubated overnight at room temperature.

4. Assay: 96-well microtiter plates (Nunc-Immunoplates, Maxisorp, Nunc Intermed Ltd, Copenhagen, Denmark) were coated overnight at room temperature in a wet chamber with 50 µl of streptavidin (ImmunoPure® Streptavidin, PIERCE) in PBS pH 7.4. After rinsing the plates with 0.15 M sodium chloride and 0.05% (w/v) Tween 20 the free binding sites of the polystyrene surface were blocked with 80 µl of 2 mg/ml bovine serum albumin (Sigma-Aldrich) in PBS, pH 7.4 for 1 hour at room temperature. Then biotinylated peptide diluted 1:10000 was added and incubated for 1 hour at room temperature.

Thirty microliters of pre-treated standard (from 1 to 125 ng/ml) and samples of synovial fluids or sera (obtained by usual puncture) were mixed with 30 µl of diluted antibody. After 1 hour preincubation at room temperature 50 µl of the mixture was added to the coated wells of the microtiter plate and further incubated for 1 hour at room temperature. The plates were rinsed as above and the bound antibodies were detected by adding 50 µl of a dilution of rabbit anti-swine IgG conjugated with alkaline phosphatase (DAKO A/S, Denmark) in 0.1 M sodium chloride, 0.05 M sodium phosphate, 0.05% Tween 20, pH 7.5 containing 2 mg/ml of BSA. After 1 hour incubation at room temperature the plates were rinsed as above and 50 µl of substrate was added (1 mg/ml p-nitrophenyl phosphate in 1M diethanolamine pH 9.8 containing 0.5 M MgCl$_2$).

The absorbance of each sample and standard was measured at 405 nm in duplicate by a microplate reader (Expert96, AsysHitech, Austria). The Mikrowin 200 software program (AsysHitech, Austria) was used to plot the calibration curve and to calculate the content of CILP-2 in the samples analyzed.

Example 4

Study Design

Twelve patients with clinically established knee joint rheumatoid arthritis according to the ACR-criteria, 12 patients with clinically established knee joint osteoarthritis according to the ACR-criteria and 12 normal control serum samples from blood donors were analyzed with the established ELISA procedure, with the results shown in FIG. 1.

The invention claimed is:

1. A peptide for differentiating osteoarthritis from rheumatoid arthritis and normal individuals without arthritis consisting of SEQ ID NO: 1.

* * * * *

UNITED STATES PATENT AND TRADEMARK OFFICE
CERTIFICATE OF CORRECTION

PATENT NO. : 7,812,125 B2
APPLICATION NO. : 11/728857
DATED : October 12, 2010
INVENTOR(S) : Pilar Lorenzo, Tore Saxne and Dick Heinegard It is certified that error appears in the above-identified patent and that said Letters Patent is hereby corrected as shown below:

Column 8, line 67
Insert the following after "FIG. 1."

--REFERENCES
1. Saxne T, Wollheim F, Pettersson H, Heinegard D. Brit. Proteoglycan concentration in synovial fluid: predictor of future cartilage destruction in rheumatoid arthritis. Med. J. (1987), 295, 1447-1448.

2. Lindqvist E, Eberhardt K, Bendtzen K, Heinegard D, Saxne T. Ann Rheum Dis. Prognostic laboratory markers of joint damage in rheumatoid arthritis. (2005) 64, 196-201.

3. Lorenzo P, Neame P, Sommarin Y, Heinegard D. Cloning and deduced amino acid sequence of a novel cartilage protein (CILP) identifies a proform including a nucleotide pyrophosphohydrolase. J Biol Chem 1998;273:23469–75.

4. Lorenzo P, Bayliss MT, Heinegard D: A novel cartilage protein (CILP) present in the mid-zone of human articular cartilage increases with age. J Biol Chem 1998;273:23463–8.

5. Lorenzo P, Aman P, Sommarin Y, Heinegard D. The human CILP gene: exon/intron organization and chromosomal mapping. Matrix Biol 1999;18:445–54.

6. Nakamura I, Okawa A, Ikegawa S, Takaoka K, Nakamura Y. Genomic organization, mapping, and polymorphisms of the gene encoding human cartilage intermediate layer protein. J Hum Genet 1999;44:203–5.

7. Tsuruha J, Masuko-Hongo K, Kato T, Sakata M, Nakamura H, Nishioka K. Implication of cartilage intermediate layer protein in cartilage destruction in subsets of patients with osteoarthritis and rheumatoid arthritis. Arthritis Rheum 2001;44:838–45.

Signed and Sealed this
Twenty-first Day of June, 2011

David J. Kappos
*Director of the United States Patent and Trademark Office*

8. Masuda I, Hamada J-l, Haas A, Ryan L, McCarty D. A unique ectonucleotide pyrophosphohydrolase associated with porcine chondrocyte-derived vesicles. J Clin Invest 1995;95:699–704.

9. Masuda I, Halligan BD, Barbieri JT, Haas AL, Ryan LM, McCarty DJ. Molecular cloning and expression of a porcine chondrocyte nucleotide pyrophosphohydrolase. Gene 1997;197:277–87.

10. Hirose J, Masuda I, Ryan LM. Expression of cartilage intermediate layer protein/nucleotide pyrophosphohydrolase parallels the production of extracellular inorganic pyrophosphate in response to growth factors and with aging. Arthritis Rheum 2000;43:2703–11.

11. Masuda I, Iyama K-l, Halligan BD, Barbieri JT, Haas AL, McCarty DJ, et al. Variations in site and levels of expression of chondrocyte nucleotide pyrophosphohydrolase with aging. J Bone Miner Res 2001;16:868–75.

12. Johnson K, Hashimoto S, Lotz M, Pritzker K, Goding J, Terkeltaub R. Up-regulated expression of the phosphodiesterase nucleotide pyrophosphatase family member PC-1 is a marker and pathogenic factor for knee meniscal cartilage matrix calcification. Arthritis Rheum 2001;44:1071–81.

13. Johnson K., Farley D., Hu S., Terkeltaub R. One of Two Chondrocyte-Expressed Isoforms of Cartilage Intermediate-Layer Protein Functions as an Insulin-Like Growth Factor 1 Antagonist. Arthritis Rheum Vol. 48, No. 5, May 2003, pp 1302–1314.

14. Du H., Masuko-Hongo K., Nakamura H., Xiang Y., Bao C-D., Wang X-D.,; Chen S-L., Nishioka K., Kato T. The prevalence of autoantibodies against cartilage intermediate layer protein, YKL-39, osteopontin, and cyclic citrullinated peptide in patients with early-stage knee osteoarthritis: evidence of a variety of autoimmune processes. Rheumatology international, (2005 Nov) Vol. 26, No. 1, pp. 35-41. Electronic Publication: 2004-09-18.

15. Kato Tomohiro; Xiang Yang; Nakamura Hiroshi; Nishioka Kusuki. Neoantigens in osteoarthritic cartilage. Current opinion in rheumatology, (2004 Sep) Vol. 16, No. 5, pp. 604-8.

16. Lorenzo P, Bayliss M, Heinegard D. Altered patterns and synthesis of extracellular matrix macromolecules in early osteoarthritis. Matrix Biol. (2004) 23, 381-91.--

SEQUENCE LISTING

<160> NUMBER OF SEQ ID NOS: 1

<210> SEQ ID NO 1
<211> LENGTH: 689
<212> TYPE: PRT
<213> ORGANISM: Homo sapiens

<400> SEQUENCE: 1

```
Arg Asp Ala Thr Pro Thr Glu Glu Pro Met Ala Thr Ala Leu Gly Leu
1               5                   10                  15

Glu Arg Arg Ser Val Tyr Thr Gly Gln Pro Ser Pro Ala Leu Glu Asp
            20                  25                  30

Trp Glu Glu Ala Ser Glu Trp Thr Ser Trp Phe Asn Val Asp His Pro
        35                  40                  45

Gly Gly Asp Gly Asp Phe Glu Ser Leu Ala Ala Ile Arg Phe Tyr Tyr
    50                  55                  60

Gly Pro Ala Arg Val Cys Pro Arg Pro Leu Ala Leu Glu Ala Arg Thr
65                  70                  75                  80

Thr Asp Trp Ala Leu Pro Ser Ala Val Gly Arg Val His Leu Asn
                85                  90                  95

Pro Thr Arg Gly Phe Trp Cys Leu Asn Arg Glu Gln Pro Arg Gly Arg
            100                 105                 110

Arg Cys Ser Asn Tyr His Val Arg Phe Arg Cys Pro Leu Glu Ala Ser
        115                 120                 125

Trp Gly Ala Trp Gly Pro Trp Gly Pro Cys Ser Gly Ser Cys Gly Pro
    130                 135                 140

Gly Arg Arg Leu Arg Arg Arg His Cys Pro Ser Pro Ala Gly Asp Ala
145                 150                 155                 160

Cys Pro Gly Arg Pro Leu Glu Ala Gln Lys Cys Val Arg Pro Arg Cys
                165                 170                 175

Pro Gly Cys Ser Leu Asp Thr Cys Glu Cys Pro Asp His Ile Leu Leu
            180                 185                 190

Gly Ser Val Val Thr Pro Ser Gly Gln Pro Leu Leu Gly Ala Arg Val
        195                 200                 205

Ser Leu Arg Asp Gln Pro Gly Thr Val Ala Thr Ser Asp Ala His Gly
    210                 215                 220

Thr Phe Arg Val Pro Gly Val Cys Ala Asp Ser Arg Ala Asn Ile Arg
225                 230                 235                 240

Ala Gln Met Asp Gly Phe Ser Ala Gly Glu Ala Gln Ala Gln Ala Asn
                245                 250                 255

Gly Ser Ile Ser Val Val Thr Ile Ile Leu Asp Lys Leu Glu Lys Pro
            260                 265                 270

Tyr Leu Val Lys His Pro Glu Ser Arg Val Arg Glu Ala Gly Gln Asn
        275                 280                 285

Val Thr Phe Cys Cys Lys Ala Ser Gly Thr Pro Met Pro Lys Lys Tyr
    290                 295                 300

Ser Trp Phe His Asn Gly Thr Leu Leu Asp Arg Arg Ala His Gly Tyr
305                 310                 315                 320

Gly Ala His Leu Glu Leu Arg Gly Leu Arg Pro Asp Gln Ala Gly Ile
                325                 330                 335

Tyr His Cys Lys Ala Trp Asn Glu Ala Gly Ala Val Arg Ser Gly Thr
            340                 345                 350
```

-continued

```
Ala Arg Leu Thr Val Leu Ala Pro Gly Gln Pro Ala Cys Asp Pro Arg
        355                 360                 365

Pro Arg Glu Tyr Leu Ile Lys Leu Pro Glu Asp Cys Gly Gln Pro Gly
        370                 375                 380

Ser Gly Pro Ala Tyr Leu Asp Val Gly Leu Cys Pro Asp Thr Arg Cys
385                 390                 395                 400

Pro Ser Leu Ala Gly Ser Ser Pro Arg Cys Gly Asp Ala Ser Ser Arg
                405                 410                 415

Cys Cys Ser Val Arg Arg Leu Glu Arg Arg Glu Ile His Cys Pro Gly
                420                 425                 430

Tyr Val Leu Pro Val Lys Val Ala Glu Cys Gly Cys Gln Lys Cys
                435                 440                 445

Leu Pro Pro Arg Gly Leu Val Arg Gly Arg Val Val Ala Ala Asp Ser
450                 455                 460

Gly Glu Pro Leu Arg Phe Ala Arg Ile Leu Leu Gly Gln Glu Pro Ile
465                 470                 475                 480

Gly Phe Thr Ala Tyr Gln Gly Asp Phe Thr Ile Glu Val Pro Pro Ser
                485                 490                 495

Thr Gln Arg Leu Val Val Thr Phe Val Asp Pro Ser Gly Glu Phe Met
                500                 505                 510

Asp Ala Val Arg Val Leu Pro Phe Asp Pro Arg Gly Ala Gly Val Tyr
                515                 520                 525

His Glu Val Lys Ala Met Arg Lys Lys Ala Pro Val Ile Leu His Thr
                530                 535                 540

Ser Gln Ser Asn Thr Ile Pro Leu Gly Glu Leu Glu Asp Glu Ala Pro
545                 550                 555                 560

Leu Gly Glu Leu Val Leu Pro Ser Gly Ala Phe Arg Arg Ala Asp Gly
                565                 570                 575

Lys Pro Tyr Ser Gly Pro Val Glu Ala Arg Val Thr Phe Val Asp Pro
                580                 585                 590

Arg Asp Leu Thr Ser Ala Ala Ser Ala Pro Ser Asp Leu Arg Phe Val
                595                 600                 605

Asp Ser Asp Gly Glu Leu Ala Pro Leu Arg Thr Tyr Gly Met Phe Ser
        610                 615                 620

Val Asp Leu Arg Ala Pro Gly Ser Ala Glu Gln Leu Gln Val Gly Pro
625                 630                 635                 640

Val Ala Val Arg Val Ala Ala Ser Gln Ile His Met Pro Gly His Val
                645                 650                 655

Glu Ala Leu Lys Leu Trp Ser Leu Asn Pro Glu Thr Gly Leu Trp Glu
                660                 665                 670

Glu Glu Ser Gly Phe Arg Arg Glu Gly Ser Ser Gly Pro Arg Val Arg
                675                 680                 685

Arg
```